US006864981B2

United States Patent
Vienot et al.

(10) Patent No.: US 6,864,981 B2
(45) Date of Patent: Mar. 8, 2005

(54) METHOD OF OBTAINING A RANGE OF COLORS

(75) Inventors: Françoise Vienot, Paris (FR); Fatima Benhalima, Paris (FR); Hans Brettel, Paris (FR)

(73) Assignees: Essilor International (Compagnie Generale d'Optique), Charenton le Pont (FR); Museum National d'Histoire Naturelle, Paris (FR)

( * ) Notice: Subject to any disclaimer, the term of this patent is extended or adjusted under 35 U.S.C. 154(b) by 428 days.

(21) Appl. No.: 10/175,075

(22) Filed: Jun. 20, 2002

(65) Prior Publication Data

US 2003/0053063 A1 Mar. 20, 2003

(30) Foreign Application Priority Data

Jun. 22, 2001 (FR) ............................................ 01 08295

(51) Int. Cl.[7] .............................................. G01N 21/25

(52) U.S. Cl. ....................................... 356/407; 356/416

(58) Field of Search ................................. 356/407, 408, 356/416, 418, 419, 420, 421, 425, 124; 250/226

(56) References Cited

U.S. PATENT DOCUMENTS 3,609,047 A * 9/1971 Marlow ....................... 356/434
3,653,771 A * 4/1972 Piringer ....................... 356/422
6,149,270 A 11/2000 Hayashi

FOREIGN PATENT DOCUMENTS

EP          0 800 096          10/1997

* cited by examiner

*Primary Examiner*—Gregory J. Toatley, Jr.
*Assistant Examiner*—Roy M. Punnoose
(74) *Attorney, Agent, or Firm*—Young & Thompson

(57) ABSTRACT

A method of obtaining a range of colors includes the following steps: selecting a test color from a predetermined set of colors, selecting a test palette comprising a plurality of color samples, measuring the real color of each sample when illuminated by a white light source, measuring the apparent color of each sample when illuminated by a test source formed by the white light source filtered by the test color, measuring the chromatic error between the real color and the apparent color of each sample, taking account of chromatic adaptation, measuring the mean chromatic error for all the chromatic errors, comparing the mean chromatic error to a test value, and adding the test color to the range if the mean chromatic error is less than or equal to the test value.

10 Claims, 8 Drawing Sheets

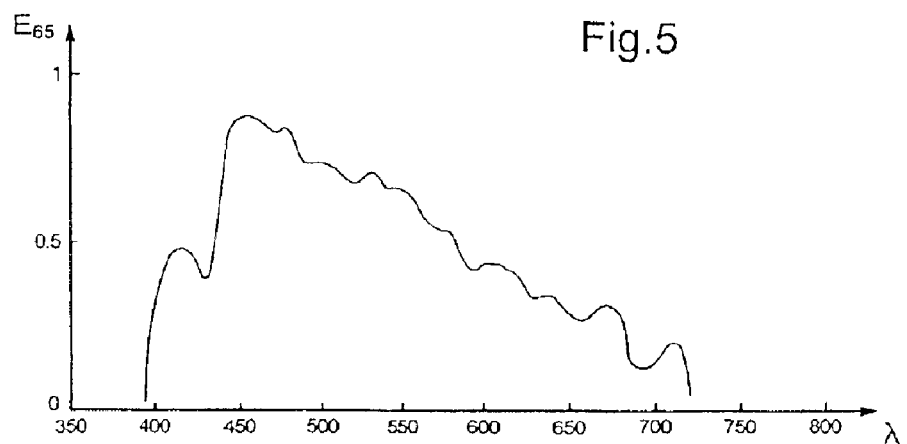
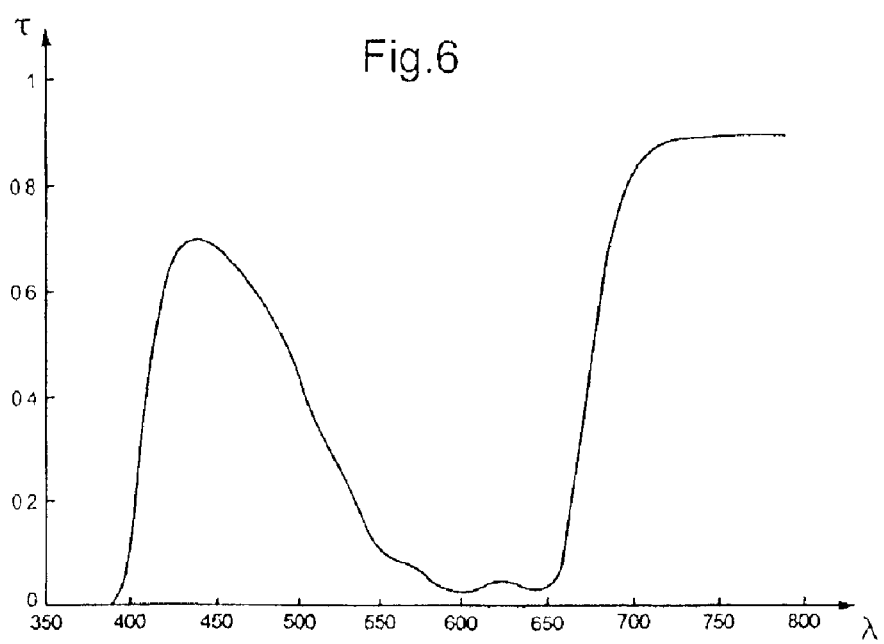

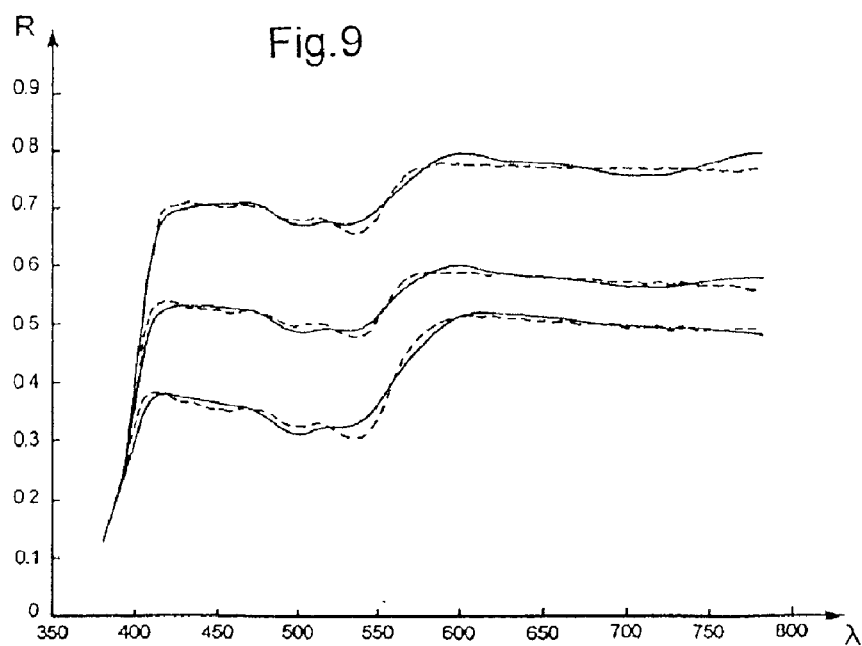
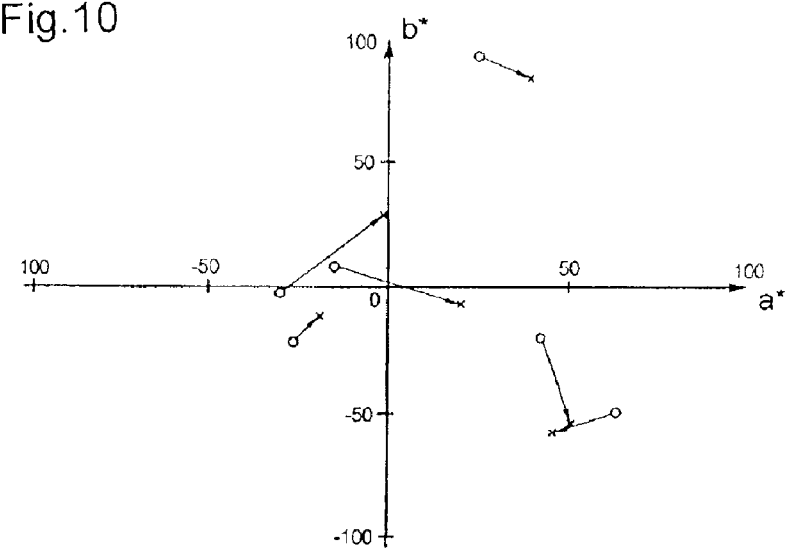

Fig.11
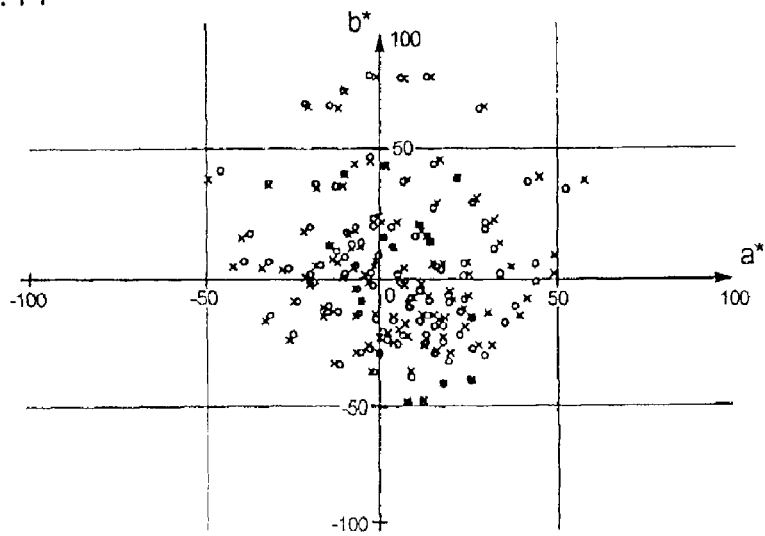
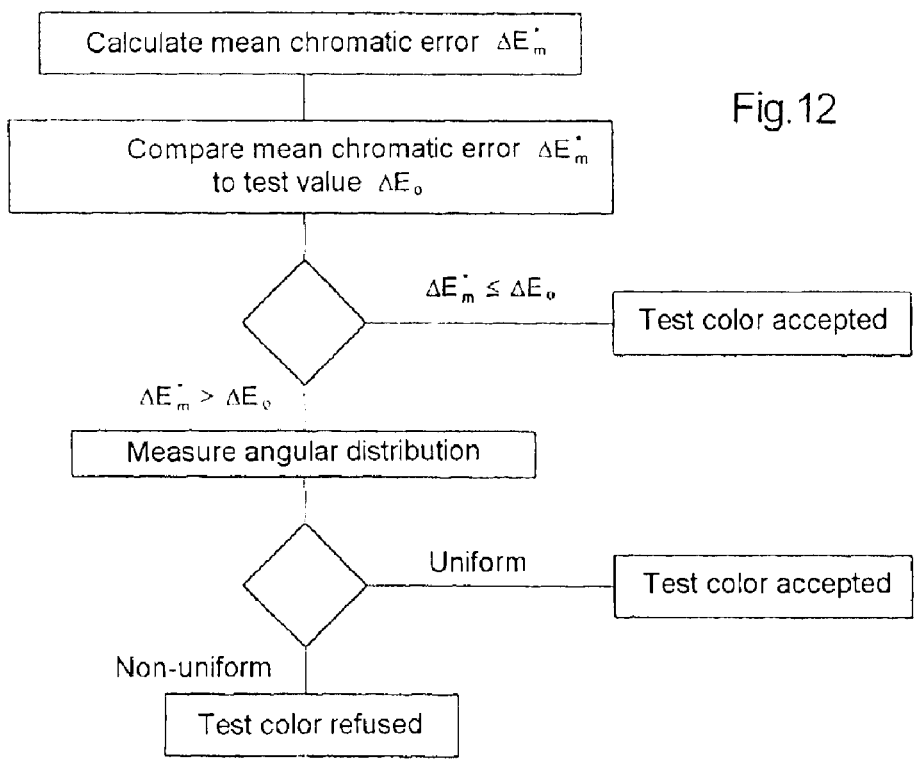
Fig.12

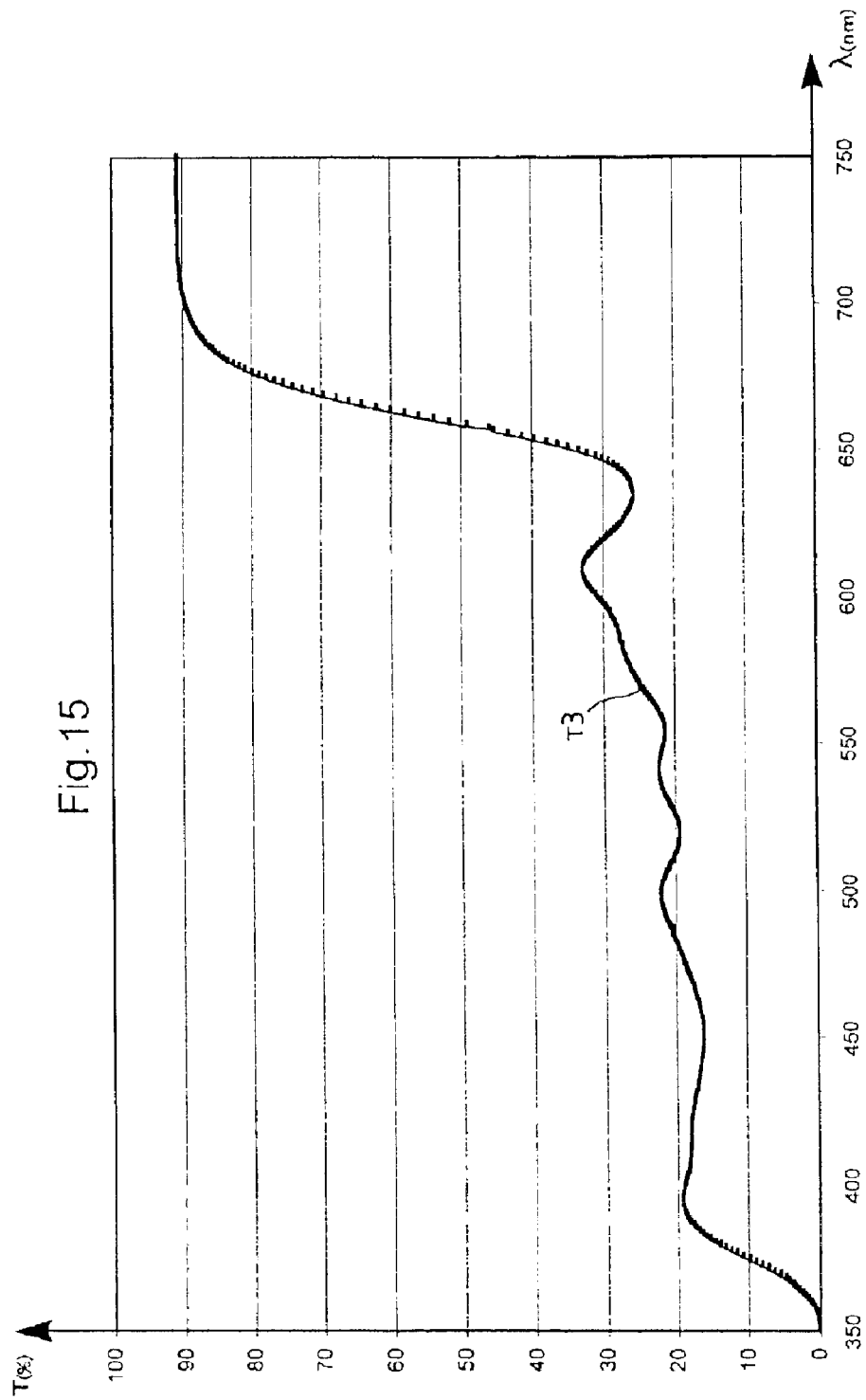

METHOD OF OBTAINING A RANGE OF COLORS

BACKGROUND OF THE INVENTION

1. Field of the Invention

The invention relates to a method of obtaining a range of colors, in particular for fabricating colored ophthalmic lenses.

2. Description of the Prior Art

The choice of colored lenses used to be dictated by the desire of the wearer to reduce perceived glare, in particular in order to relieve the retina in bright sunlight.

Responding to fashion trends, today's wearers are turning to ophthalmic lenses whose color is chosen merely as a matter of taste, and generally independently of their capacity to reduce glare.

Opticians' displays are therefore featuring more and more so-called "sunglasses", although this name is now not appropriate, with lenses of increasingly varied colors: yellow, green, blue, red, etc.

Wearing colored ophthalmic lenses modifies the colors perceived by the wearer, even if the wearer adapts naturally to the color of the lenses.

At present, the manufacture of a colored ophthalmic lens takes account only of its final intrinsic appearance, without concern as to the effect of wearing it on the modified appearance of colors.

The invention aims to overcome this insufficiency by proposing a method of obtaining a range of colors which, when applied in particular to fabricating a colored ophthalmic lens, takes account of its effect on the modified appearance of colors.

SUMMARY OF THE INVENTION

To this end, a first aspect of the invention proposes a method of obtaining a range of colors, including the following steps:

selecting a test color from a predetermined set of colors, selecting a test palette comprising a plurality of color samples, measuring the real color of each sample when illuminated by a white light source, measuring the apparent color of each sample when illuminated by a test source formed by the white light source filtered by the test color, measuring the chromatic error between the real color and the apparent color of each sample, taking account of chromatic adaptation, measuring the mean chromatic error for all the chromatic errors, comparing the mean chromatic error to a test value, and adding the test color to the range if the mean chromatic error is less than or equal to the test value.

In one embodiment of the invention the test color is added to the range if and only if each chromatic error is less than or equal to the test value.

In another embodiment of the invention the method includes the following steps if at least one chromatic error is greater than the test value:

measuring the angular distribution of the calorimetric deviations between the real color and the apparent color of each sample, and adding the test color to the range if the angular distribution is uniform.

The set comprises the Munsell atlas, for example, and the test palette comprises a plurality of color samples chosen from the Munsell atlas, or a plurality of samples whose colors are most representative of the Munsell space.

The apparent color and the real color are measured by calculating their coordinates in a predetermined chromatic space, such as the CIELAB space.

A second aspect of the invention provides a range of more than two colors obtained by the above method.

A third aspect of the invention provides a method of obtaining a colored ophthalmic lens, including a step of selecting a color from the above range or obtained by the above method.

Other features and advantages of the invention will become apparent in the light of the following description of one embodiment of the invention, which is given by way of non-limiting example and with reference to the accompanying drawings.

BRIEF DESCRIPTION OF THE DRAWINGS

FIG. 5 is a graph representing the spectral energy distribution of the $D_{65}$ light source.

FIG. 6 is a graph showing the transmission factor of a blue lens as a function of the wavelength of the incident light.

FIG. 9 is a graph representing the reflection factor of three color samples as a function of the wavelength of the incident light with which they are illuminated.

FIG. 10 is a representation of a plane chromatic space a* b* showing, by circles, the so-called real colors of the six samples from FIG. 8, when illuminated by a white source, and, by crosses, the so-called apparent colors of the six samples when illuminated by a test source formed by the filtered white source; the calorimetric deviation vectors linking the circle and the cross relating to each color are also shown in this chromatic space.

FIG. 11 is a representation of a plane chromatic space a* b* showing, by circles, the so-called real colors of 127 samples when illuminated by a white source and, by crosses, the so-called apparent colors of the 127 samples when illuminated by a test source formed by the filtered white source.

FIG. 12 is a diagram showing steps of a method according to the invention.

FIGS. 13, 14 and 15 are graphs representing the spectral distributions of the transmission factors of three colored lenses.

DETAILED DESCRIPTION OF THE PREFERRED EMBODIMENTS

Figure 1:
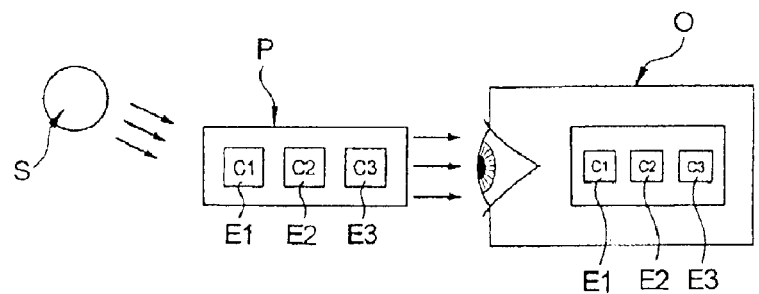
FIG. 1 is a diagrammatic view showing a palette comprising a plurality of color samples illuminated by a white source and viewed by an observer.

FIG. 1 shows a palette P comprising a plurality of samples E1, E2, E3 of respective different real colors C1, C2, C3.

When the palette P is illuminated by a white light source S that is supposedly ideal, i.e. similar to natural daylight, for example in sunshine or under a cloudless sky, in the north, an observer O, also supposedly ideal, i.e. suffering from no chromatic aberrations or ametropia, who is viewing the palette 2, perceives a representation thereof, referred to as the perceived palette, whose samples represent respective colors identical to the real colors C1, C2, C3 of the samples E1, E2, E3.

Figure 2:
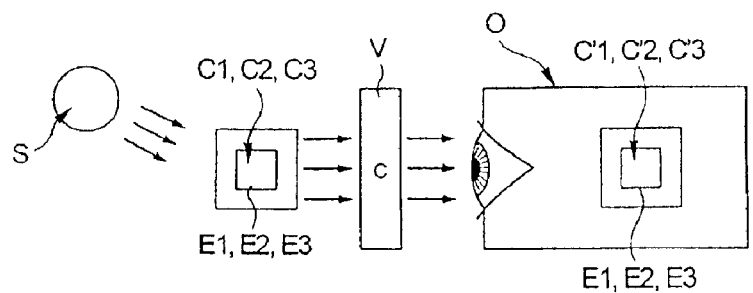
FIG. 2 is a diagrammatic view showing one of the samples from the FIG. 1 palette, illuminated by the same white source, with a colored lens between the observer and the palette.

If a colored ophthalmic lens V of color C is placed between the observer O and any one of the samples E1, E2 or E3 of the palette P, that sample assumes for the observer O a color C'1, C'2, C'3 different from its real color (FIG. 2).

Figure 3:
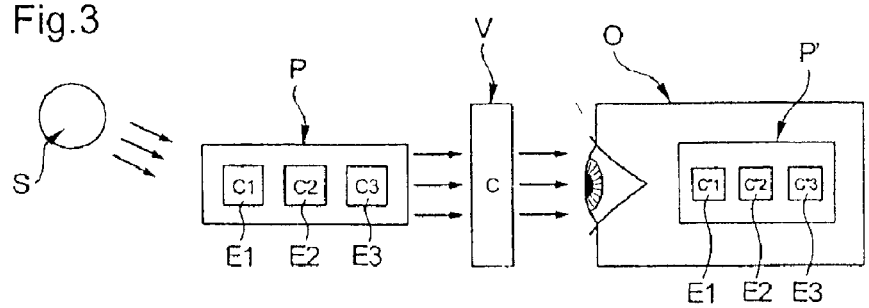
FIG. 3 is a view similar to FIG. 1, with the colored lens from FIG. 2 between the palette and the observer.

On the other hand, if the same colored ophthalmic lens V is placed between the observer O and the whole of the palette P (FIG. 3), each sample has for the observer a color C"1, C"2, C"3 that is not only different from its real color but also from the perceived color C'1, C'2, C'3 when the lens V is placed in front of only one sample E1, E2 or E3.

Accordingly, for the observer O, the distortion of the colors caused by the lens V for each sample E1, E2, E3 varies as a function of the visual area covered by the lens V. This is explained by the chromatic adaptation faculties of the visual system of the observer O, comparable to a balance of whites. The change from the real colors C1, C2, C3 to the perceived colors C"1, C"2, C"3 due to the colored lens is called calorimetric deviation.

At present, when choosing colored ophthalmic lenses, the calorimetric deviation is left to the judgement of the wearer, and is therefore subjective, even though some lens colors can cause a calorimetric deviation that is objectively unacceptable, in particular in the case of perception of colors conforming to a code or a standard, for example in connection with safety signals.

The aim is to draw up a range of colors that can be used for the manufacture of ophthalmic lenses whose effect on calorimetric deviation when employed to filter a predefined white light source is acceptable in accordance with objective criteria that emerge hereinafter.

Note first of all that, for the observer, whether the lens is between the source and the palette or between the palette and the observer is immaterial.

Figure 4:
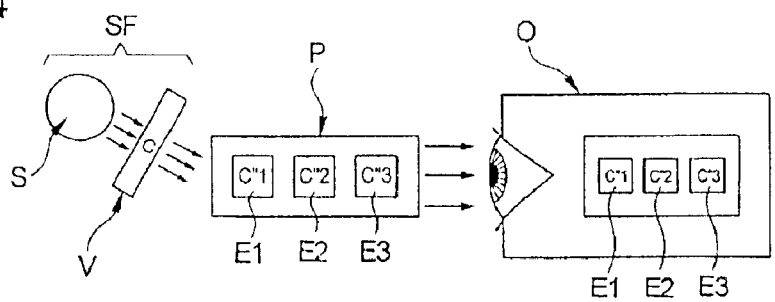
FIG. 4 is a view similar to FIG. 3 with the lens between the white source and the palette.

Consequently, placing the lens V between the palette P and the observer O has the same effect as illuminating the palette P with a colored source SF formed by the white source S filtered by the colored lens V (FIG. 4). The filtered source is referred to as the test source hereinafter.

Provided that the chromatic adaptation faculties of the visual system are taken into account, it is therefore possible to obtain the required range of colors by a method that does not necessitate the intervention of an observer.

A first step consists of choosing the test source, that is to say, on the one hand, the white source and, on the other hand, the color employed to filter it, which is referred to as the test color hereinafter.

The white source is chosen from ideal white sources. In a preferred embodiment of the invention, the white source is the $D_{65}$ light source defined by the International Commission on Illumination, which is well-known to the person skilled in the art and has a color temperature equal to approximately 6 500 K.

Figure 7:
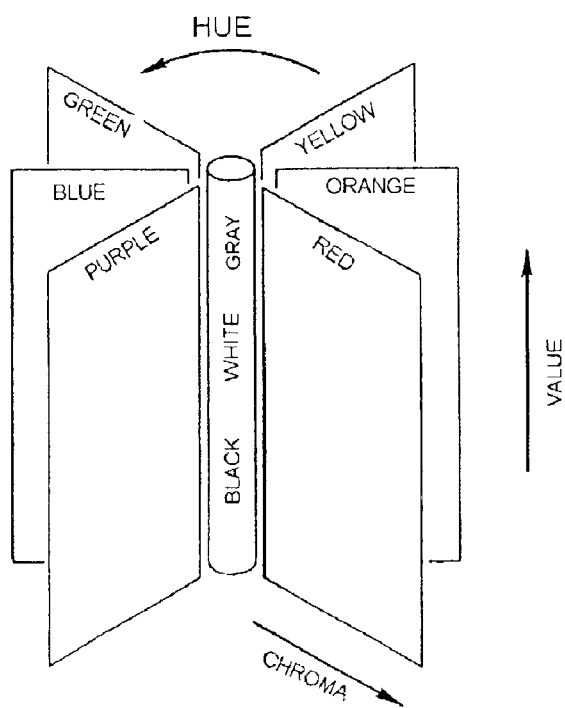
FIG. 7 is a cylindrical diagrammatic representation of the Munsell space.

The test color is chosen from a set of predetermined colors that are preferably representative of all the colors of the visible spectrum. In one embodiment of the invention, this set is the Munsell color atlas, which takes the form of a cylindrical array in which the colors are classified in accordance with the following three criteria: hue, value and chroma. FIG. 7 is a cylindrical diagrammatic representation of the Munsell atlas, which is well-known to the person skilled in the art.

The atlas provides more than a thousand color samples (in fact 1 269 samples).

Each sample, and consequently each color, from the Munsell atlas can be characterized by the spectral distribution of its transmission factor, i.e. the spectral distribution of the transmission factor of a lens of the color concerned. This distribution comprises all of the transmission factors of the colored lens for a range of wavelengths from 350 nm to 750 nm, which corresponds closely to the spectrum visible to the human eye (1 nm=$10^{-9}$ m).

The transmission factor of a given object (in this instance the lens) when illuminated by an incident luminous flux is a dimensionless magnitude with a value from 0 to 1, or from 0% to 100% if expressed as a percentage, equal to the ratio of the transmitted luminous flux to the incident luminous flux (multiplied by a factor of 100 if expressed as a percentage).

Accordingly, for a step of 1 nm, each sample, and consequently the corresponding color, can be characterized by a set of 401 reflection factors. For each color, it is therefore possible to construct from this set a curve representing the spectral distribution of its reflection factor, as shown in FIGS. 6, 13, 14 and 15, for blue, gray, green and brown colors, respectively.

Using the white source and the chosen test color, it is then possible to characterize the test source: from the spectral energy distribution $E_{65}(\lambda)$ of the white light source (in this instance the $D_{65}$ light source, see FIG. 5) and the spectral transmission factor $\tau(\lambda)$ of the test color, the spectral energy distribution $E_K(\lambda)$ of the test source is determined, this energy being equal to the product of the energy $E_{65}(\lambda)$ of the white light source and the transmission factor $\tau(\lambda)$ associated with the test color:

$$E_K(\lambda)=\tau(\lambda)E_{65}(\lambda)$$

The next step is to calculate, taking account of chromatic adaptation, the calorimetric deviation caused by the test source on a palette referred to hereinafter as the test palette, comprising a plurality of color samples that are sufficiently representative of the whole of the visible spectrum, in order to model visual situations that an observer is likely to encounter in daily life.

The test palette can be based on the Munsell atlas, which conforms to this requirement.

As stated above, each sample, and consequently each color, from the Munsell atlas can be characterized by the spectral distribution of its transmission factor.

Each sample, respectively each color, can also be characterized by the spectral distribution of its reflection factor. This distribution comprises all of the reflection factors of the sample for a range of wavelengths from 350 nm to 750 nm, for example, which correspond closely to the spectrum visible to the human eye (1 nm=$10^{-9}$ m).

The reflection factor of a given sample illuminated by an incident luminous flux is a dimensionless magnitude from 0 to 1, or from 0% to 100% if expressed as a percentage, and equal to the ratio of the reflected luminous flux to the incident luminous flux, multiplied by a factor of 100 if expressed as a percentage.

The number of reflection factors characteristic of each sample depends on the chosen step between two adjacent wavelengths in the range of wavelengths.

Accordingly, for a step of 5 nm, each sample is characterized by a set of 81 reflection factors.

For a wavelength step of 5 nm, the Munsell atlas can therefore be represented algebraically by a Munsell matrix X comprising 1 269 rows and 81 columns, each row corresponding to a sample and containing all of the reflection factors thereof for the chosen range.

These reflection factors can be measured directly by spectrophotometry, but the person skilled in the art can obtain their values from the Computer Science and Physics Department of the University of Joensuu, Finland.

Of course, the Munsell space could itself constitute the test palette. However, given the size of the Munsell matrix X, this implies very long computations, requiring very costly data processing or electronic systems.

It is therefore preferable to employ a test palette of reduced size. Let N denote the number of samples on the test palette, each sample and its corresponding color being both identified by an integer index i from 1 to N.

Accordingly, in a first embodiment of the invention, the test palette comprises 127 samples (N=127) extracted from the Munsell atlas by selecting one sample in ten. Of course, it would be possible to select one sample in five, for example, or, conversely, one sample in twenty, depending on the available computation power.

In a second embodiment of the invention, the test palette is constructed by compressing the Munsell atlas in order to extract the most significant color tendencies.

This compression is effected by reducing the Munsell matrix X using the method known as principal component analysis (PCA).

The PCA method includes the following steps:

calculating a correlation matrix C equal to the product of the transposed matrix $^tX$ of the calculation matrix X by the matrix X itself:

$$C = {}^tXX, \text{ and}$$

calculating the eigenvalues and eigenvectors of the correlation matrix C, which is symmetrical by definition.

Each eigenvector, which takes the form of a column of 81 components each corresponding to a wavelength, is representative of an eigencolor.

The test palette can comprise a set of 81 samples (N=81) in which the color of each sample is a respective eigencolor.

The eigenvalue associated with each of the eigencolors corresponds to its inertia, i.e. the representativeness of the eigencolor with respect to all of the colors from the Munsell atlas.

For each eigencolor i, the weight $W_i$ of its eigenvalue $\alpha_i$ is given by the following equation:

$$W_i = \frac{\alpha_i}{\sum_{i=1}^{N} \alpha_i}$$

The test palette can equally comprise a subset of samples whose colors are chosen from the eigencolors of higher weight.

To this end, the eigenvectors are classified in decreasing order of their respective eigenvalues, i.e. from the eigenvector having the highest eigenvalue to the eigenvector having the lowest eigenvalue.

It is found that the first six eigenvectors taken together account for approximately 80% of the total inertia of all of the eigenvectors, and that consequently the first six eigenvectors provide an acceptable representation of the color tendencies of the Munsell atlas.

The first six eigenvectors are therefore selected, i.e. the six eigenvectors having the highest eigenvalues (N=6).

The test palette therefore comprises six colors with the highest weights: it can be represented, algebraically, by a matrix constituted by juxtaposing six associated eigenvectors.

Figure 8:
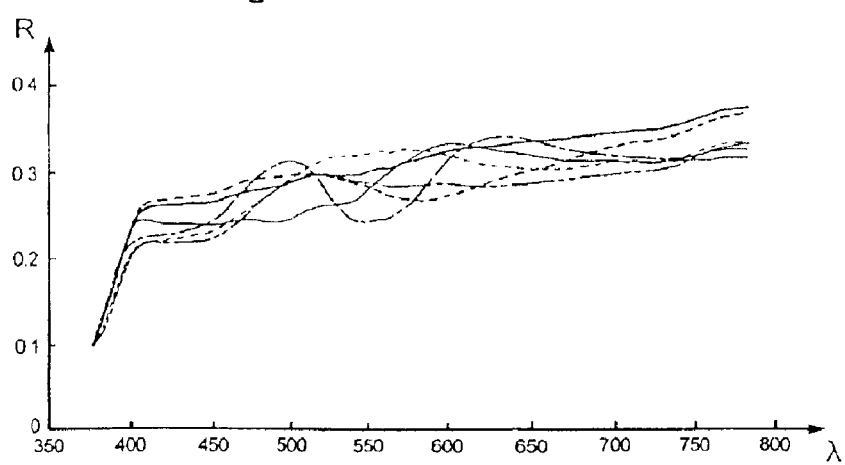
FIG. 8 is a graph representing the reflection factor of six color samples as a function of the wavelength of the incident light with which they are illuminated.

The FIG. 8 graph shows these first six eigenvectors, in the form of curves of the type R=f(λ), where R is the reflection factor and λ is the wavelength.

As is clear from this figure, the eigencolors corresponding to the first six eigenvectors are pastel colors.

Note that for each wavelength λ, it is possible to arrive at an approximation of the reflection factor of each sample from the Munsell atlas on the basis of the first six eigenvectors, using the following equation:

$$R(\lambda) = \sum_{i=1}^{i=N} \sqrt{\alpha_i}\, W_i(\alpha_i) V_i(\lambda) \tag{1}$$

in which λ is the wavelength concerned, $V_i(\lambda)$ the component of the $i^{th}$ eigenvector for the wavelength λ, $\alpha_i$ the associated eigenvalue and $W_i$ the weight thereof.

The FIG. 9 graph shows, in full line and in dashed line, the curves of the reflection factors of three color samples from the Munsell atlas as a function of the wavelength of the incident light, these factors being obtained by means of the above equation (1), respectively with N=6 and N=81, and shows that reflection factors corresponding to N=6 are an acceptable approximation of the reflection factors corresponding to N=81.

Once the test palette has been constructed, the real color of each of its samples is measured, in other words the color of the sample when illuminated by a white light source, in this instance the $D_{65}$ light source, after which its apparent color is measured, i.e. its color when illuminated by the test source.

In a preferred embodiment of the invention, these measurements are effected at least in part using the International Commission on Illumination CRI-96 method.

The calculations carried out to measure the apparent color of a given sample i include the following steps:

a) Calculating trichromatic coordinates $(X_k, Y_k, Z_k)$ of the test source in the space CIEXYZ, as defined by the International Commission on Illumination, from its relative spectral energy distribution $E_k(\lambda)$, as defined above;

b) Calculating trichromatic coordinates in the space CIEXYZ of the white light source which is chosen so that its chromaticity is as close as possible to the chromaticity of the test source, which in this instance is the $D_{65}$ light source;

c) Calculating trichromatic coordinates $(X_i, Y_i, Z_i)$ in the space CIEXYZ of the color i when illuminated by the test source;

d) Converting from the trichromatic coordinates $X_i, Y_i, Z_i$ of the system CIEXYZ to the spectral coordinates $R_i, G_i, B_i$ of the RGB system, as defined by the International Commission on Illumination, using the following equations:

$R_i = 0.040024 X_i + 0.70760 Y_i - 0.0808 Z_i$ $G_i = -0.22630 X_i + 1.16532 Y_i + 0.04570 Z_i$ $B_i = 0.91822 Z_i$ e) Converting the test source into a reference source and calculating, for the color when illuminated by the reference source, its spectral coordinates $R_{Di}$, $G_{Di}$, $B_{Di}$ in the RGB system:

$$R_{Di} = (20\xi_D + 1)\left[\frac{R_i + 1}{20\xi + 1}\right]^{\frac{\beta_1(R_0)}{\beta_1(R_{0D})}} - 1$$

$$G_{Di} = (20\eta_D + 1)\left[\frac{G_i + 1}{20\eta + 1}\right]^{\frac{\beta_1(G_0)}{\beta_1(G_{0D})}} - 1$$

$$B_{Di} = (20\zeta_D + 1)\left[\frac{B_i + 1}{20\zeta + 1}\right]^{\frac{\beta_2(B_0)}{\beta_2(B_{0D})}} - 1$$

in which:

$$\xi = \frac{0.48105X_k + 0.78841Y_k - 0.08081}{Y_k}$$

$$\eta = \frac{-0.27200X_k + 1.11962Y_k + 0.04570}{Y_k}$$

$$\zeta = 0.91822\frac{1 - X_k - Y_k}{Y_k}$$

and:

$$\xi_D = \frac{0.48105X_D + 0.78841Y_D - 0.08081}{Y_D}$$

$$\eta_D = \frac{-0.27200X_D + 1.11962Y_D + 0.04570}{Y_D}$$

$$\zeta_D = 0.91822\frac{1 - X_D - Y_D}{Y_D}$$

$X_D$, $Y_D$ are the trichromatic coordinates of the reference source. Here, the reference source is chosen to be identical to the $D_{65}$ light source, for which $\xi_D = \eta_D = \zeta_D = 1$.

$R_0$, $G_0$, $B_0$ and $R_{0D}$, $G_{0D}$, $B_{0D}$ are the coordinates in the RGB system of the test source and the $D_{65}$ light source, characteristic of the chromatic adaptation:

$$\begin{vmatrix} R_0 \\ G_0 \\ B_0 \end{vmatrix} = 0.2\frac{E_0}{\pi}\begin{vmatrix} \xi \\ \eta \\ \zeta \end{vmatrix} \quad \text{and} \quad \begin{vmatrix} R_{0D} \\ V_{0D} \\ B_{0D} \end{vmatrix} = 0.2\frac{E_0}{\pi}\begin{vmatrix} \xi_D \\ \eta_D \\ \zeta_D \end{vmatrix}$$

where $E_0$ and $E_{0D}$ are the respective luminances of the test source and the $D_{65}$ light source, such as $E_0 = E_{0D} = 1\,000$ lux, and the factor 0.2 is the luminance factor of gray.

The functions $\beta$ are defined by the following equations:

$$\beta_1(R_0) = \frac{6.469 + 6.362R_0^{0.4495}}{6.469 + R_0^{0.4495}}$$

$$\beta_1(G_0) = \frac{6.469 + 6.362G_0^{0.4495}}{6.469 + G_0^{0.4495}}$$

$$\beta_2(B_0) = \frac{8.414 + 8.0911B_0^{0.5128}}{8.414 + B_0^{0.5128}}$$

$$\beta_1(R_{0D}) = \beta_1(G_{0D}) = 3.6810$$

$$\beta_2(B_{0D}) = 3.5656$$

f) Converting from the spectral coordinates $R_{Di}$, $G_{Di}$, $B_{Di}$ of the RGB system to the trichromatic coordinates $X_{Di}$, $Y_{Di}$, $Z_{Di}$ using the following equations:

$$X_{Di} = 1.85995R_{Di} - 1.12939G_{Di} + 0.21990B_{Di}$$

$$Y_{Di} = 0.36119R_{Di} + 0.63881G_{Di}$$

$$Z_{Di} = 1.08906B_{Di}$$

g) Converting from the trichromatic coordinates $X_{Di}$, $Y_{Di}$, $Z_{Di}$ to the coordinates $a^*_{ki}$, $a^*_{ki}$, $b^*_{ki}$ in the space CIELAB, as defined by the International Commission on Illumination, using the following equations:

$$L^*_{ki} = 116\left(\frac{Y_{Di}}{Y_n}\right)^{\frac{1}{3}} - 16 \quad \text{if} \quad \frac{Y_{Di}}{Y_n} > 0.008856$$

$$L^*_{ki} = 903.3\left(\frac{Y_{Di}}{Y_n}\right) \quad \text{if} \quad \frac{Y_{Di}}{Y_n} \leq 0.008856$$

$$a^*_{ki} = 500\left[f\left(\frac{X_{Di}}{X_n}\right) - f\left(\frac{Y_{Di}}{Y_n}\right)\right]$$

$$b^*_{ki} = 200\left[f\left(\frac{Y_{Di}}{Y_n}\right) - f\left(\frac{Z_{Di}}{Z_n}\right)\right]$$

in which the functions f are defined as follows:

$$f\left(\frac{X}{X_n}\right) = \left(\frac{X}{X_n}\right)^{\frac{1}{3}} \quad \text{if} \quad \frac{X}{X_n} > 0.008856$$

$$f\left(\frac{X}{X_n}\right) = 7.787\left(\frac{X}{X_n}\right) + \frac{16}{116} \quad \text{if} \quad \frac{X}{X_n} \leq 0.008856$$

$$f\left(\frac{Y}{Y_n}\right) = \left(\frac{Y}{Y_n}\right)^{\frac{1}{3}} \quad \text{if} \quad \frac{Y}{Y_n} > 0.008856$$

$$f\left(\frac{Y}{Y_n}\right) = 7.787\left(\frac{Y}{Y_n}\right) + \frac{16}{116} \quad \text{if} \quad \frac{Y}{Y_n} \leq 0.008856$$

$$f\left(\frac{Z}{Z_n}\right) = \left(\frac{Z}{Z_n}\right)^{\frac{1}{3}} \quad \text{if} \quad \frac{Z}{Z_n} > 0.008856$$

$$f\left(\frac{Z}{Z_n}\right) = 7.787\left(\frac{Z}{Z_n}\right) + \frac{16}{116} \quad \text{if} \quad \frac{Z}{Z_n} \leq 0.008856$$

$X_n$, $Y_n$, $Z_n$ are the trichromatic coordinates of the color white when illuminated by the $D_{65}$ light source.

The calculations of steps c) through g) are effected for each sample of the test palette, and for perfect white if it is not included in the test palette.

The space CIELAB has the advantage of being uniform for human vision. The axis L* represents the value, from 0 for black to 100 for perfect white, and the axes a* and b* represent the chromaticity, respectively for the pairs of opposites green (a*=−100)–red (a*=+100) and blue (b*=−100)–yellow (b*=100).

The above calculations are also effected to measure the real color of the samples, steps c) through g) being repeated for each sample of the test palette and for the perfect white, each illuminated by the ideal source (i.e. the $D_{65}$ light source). $L^*_{id,i}$, $a^*_{id,i}$, $b^*_{id,i}$ are the coordinates of the colors of the samples of the test palette in the space CIELAB when illuminated by a white source.

It is then possible to obtain, in the CIELAB system and for each of the colors i, a so-called deviation vector characteristic of the calorimetric deviation (FIG. 8) and having the following coordinates:

$$L^*_{vi} = L^*_{ki} - L^*_{id,i}$$

$$a^*_{vi} = a^*_{ki} - a^*_{id,i}$$

$$b^*_{vi} = b^*_{ki} - b^*_{id,i}$$

The deviation vector is then corrected to compensate for chromatic adaptation, by subtracting the deviation vector of perfect white from the deviation vector of each sample of the test palette.

A corrected deviation vector is therefore obtained for each sample of the test palette with coordinates $L^*_{ci}$, $a^*_{ci}$, $b^*_{ci}$ in the space CIELAB, such as:

$$L^*_{ci} = L^*_{vi} - L^*_{vwhite}$$

$$a^*_{ci} = a^*_{vi} - a^*_{vwhite}$$

$$b^*_{vi} = b^*_{vi} - b^*_{vwhite}$$

in which $L^*_{vwhite}$, $a^*_{vwhite}$, $b^*_{vwhite}$ are the coordinates in the CIELAB space of the deviation vector of perfect white.

The coordinates of the corrected deviation vector thus constitute a measurement, for each sample i of the test palette, of the calorimetric deviation caused by the test source, allowing for chromatic adaptation.

The chromatic error $\Delta E^*_{ab,i}$ for each sample i is equal to the modulus of the corrected deviation vector:

$$\Delta E^*_{ab,i} = \sqrt{L^{*2}_{ci} + a^{*2}_{ci} + b^{*2}_{ci}}$$

In a different embodiment, no account is taken of value variations, but only of chromaticity, so that the chromatic error is defined by the modulus of the projection of the corrected deviation vector in the space $a^* b^*$:

$$\Delta E^*_{ab,i} = \sqrt{a^* hdci^2 + b^{*2}_{ci}}$$

The mean chromatic error $\Delta E^*_m$, is then calculated; it is equal to the arithmetical mean of all the chromatic errors $\Delta E^*_{ab,i}$:

$$\Delta E^*_m = \frac{1}{N} \sum_{i=1}^{N} \Delta E^*_{ab,i}$$

The value of the mean chromatic error $\Delta E^*_m$, is then compared to a predetermined test value $\Delta E_o$, which constitutes a first criterion for acceptance of the test color from the range.

Accordingly, if the value of the global chromatic error $\Delta E^*_m$ is less than or equal to the test value $\Delta E_o$, the test color is accepted, i.e. added to the range.

In one embodiment of the invention, the test value $\Delta E_o$ is chosen to be equal to 10. It is preferably chosen to be equal to 5.

If the value of the global chromatic error $\Delta E^*_m$ exceeds the test value $\Delta E_o$, then the test color is refused, i.e. excluded from the range.

As an alternative to this, the test color is not refused at this stage. Instead, the angular distribution of the calorimetric deviation in the space $a^* b^*$ is measured.

To this end, a deviation angle is measured for each sample i, formed by the projection in the space $a^* b^*$ of the corrected deviation vector with the axis $a^*$ or the axis $b^*$. The value $\theta_{vi}$ of this angle is provided for the axis $a^*$ by the following equation:

$$\theta_{vi} = \text{Arctan} \frac{b^*_{ci}}{a^*_{ci}}$$

and that for the axis $b^*$ by the following equation:

$$\theta_{vi} = \text{Arctan} \frac{a^*_{ci}}{b^*_{ci}}$$

The arithmetic mean of the angular distribution is then calculated, i.e. all of the deviation angles, followed by the standard deviation of the angular distribution, the standard deviation providing the measurement referred to above of the angular distribution. If the angular distribution is uniform, the test color is accepted. Otherwise, it is refused.

In one embodiment, the angular distribution is declared uniform if its standard deviation is less than 60°, preferably less than 55°.

FIG. 11 shows the $a^* b^*$ space into which have been transferred, as shown by circles, the coordinates of 127 colors of the test palette previously defined for the first embodiment, when illuminated by the $D_{65}$ light source, and, as shown by crosses, their coordinates when illuminated by the test source formed by the $D_{65}$ light source filtered by a glass whose color is characterized by the spectral energy distribution shown in FIG. 6, taking account of chromatic adaptation.

FIG. 10 shows the $a^* b^*$ space into which have been transferred, as shown by circles, the coordinates of six eigencolors of the test palette previously defined in the second embodiment, when illuminated by the $D_{65}$ light source, and, as shown by crosses, their coordinates when illuminated by the test source formed of the $D_{65}$ light source, assumed to be filtered by the same lens as above and taking account of chromatic adaptation.

This figure also shows, as arrows, the six associated corrected deviation vectors, connecting the circles to the crosses. For each eigencolor, the associated chromatic error in the $a^* b^*$ space is equal to the length of the corresponding corrected deviation vector.

In a different embodiment of the invention, the first criterion for accepting the test color is based on the mean color rendition index $R96_a$ of the test source, compared to a test value $R96_0$.

The mean color rendition index $R96_a$ is given by the following equation:

$$R96_a = \frac{1}{N} \sum_{i=1}^{6} R96_i,$$

in which $R96_1$ is the color rendition index for the test source for each color i of the test palette, in turn supplied by the following equation:

$$R96_i = 100 - c \Delta E^*_{ab,i}$$

where c=3.2562.

The test value $R96_0$ is chosen to be equal to 85, for example, or preferably 90.

The FIG. 12 diagram illustrates the principle of accepting or refusing a test color for the range.

It is therefore possible to constitute a range of colors from a predetermined set by repeating the above operations until the number of colors required for the range is obtained.

That number is left to the judgement of the person skilled in the art; nevertheless, to provide a concrete example, it is possible to constitute a range of colors whose hues are separate: for example six colors with fundamental hues: a green, a blue, a purple, a red, an orange, a yellow, or a range of colors with the same hue but different chromas and values: for example, a dozen blues of greater or lesser chroma and brightness.

Once the required final color of the lens is known, it is obtained by mixing primary coloring agents. In one embodiment of the invention the concentration of each primary coloring agent is calculated using the subtractive mixing method well known to the person skilled in the art. It is then possible to manufacture the lens, after selecting its color from the color range established in the manner previously described.

Three acceptable test colors are provided at present, with respective gray, green and brown hues, and which thus form a range as defined by the invention.

Each color can be characterized by the spectral distribution of its transmission factor τ 1(λ), expressed as a percentage and as a function of the wavelength λ of the incendent light, expressed in nanometers (nm).

The respective spectral distributions of the three colors of gray, green and brown hue previously cited and respectively denoted GRAY, GREEN and BROWN, are given by the following tables of values.

| GRAY | |
|---|---|
| Wavelength λ (nm) | Transmission factor τ 1 (%) |
| 350 | 0.151694625 |
| 351 | 0.206969129 |
| 352 | 0.263616063 |
| 353 | 0.341560226 |
| 354 | 0.435973016 |
| 355 | 0.595800287 |
| 356 | 0.785995527 |
| 357 | 0.996956708 |
| 358 | 1.298629716 |
| 359 | 1.649411527 |
| 360 | 2.144257282 |
| 361 | 2.711832274 |
| 362 | 3.419099229 |
| 363 | 4.028315894 |
| 364 | 4.685020735 |
| 365 | 5.430495265 |
| 366 | 6.247534403 |
| 367 | 7.168632636 |
| 368 | 8.027566852 |
| 369 | 9.254469087 |
| 370 | 10.6302534 |
| 371 | 12.08396857 |
| 372 | 13.55805465 |
| 373 | 14.95109773 |
| 374 | 16.17059236 |
| 375 | 17.46510848 |
| 376 | 18.70391852 |
| 377 | 19.83943138 |
| 378 | 20.93915208 |
| 379 | 22.01115257 |
| 380 | 23.01171396 |
| 381 | 23.93718868 |
| 382 | 24.79082183 |
| 383 | 25.54678394 |
| 384 | 26.24337578 |
| 385 | 26.90313523 |
| 386 | 27.51481596 |
| 387 | 28.06856778 |
| 388 | 28.59218398 |
| 389 | 29.08606938 |
| 390 | 29.40466351 |
| 391 | 29.80119144 |
| 392 | 30.15091518 |
| 393 | 30.55737226 |
| 394 | 30.84917168 |
| 395 | 31.10049734 |
| 396 | 31.42079566 |
| 397 | 31.61423652 |
| 398 | 31.88712611 |
| 399 | 32.24008281 |
| 400 | 32.41756083 |
| 401 | 32.65591012 |
| 402 | 32.93345185 |
| 403 | 33.21313361 |
| 404 | 33.38474983 |
| 405 | 33.6823143 |
| 406 | 34.13360388 |
| 407 | 34.32195772 |
| 408 | 34.5226446 |
| 409 | 34.86624106 |

-continued

| | |
|---|---|
| 410 | 35.21047366 |
| 411 | 35.58333449 |
| 412 | 35.80562537 |
| 413 | 36.16191166 |
| 414 | 36.46660816 |
| 415 | 36.79931779 |
| 416 | 37.15259937 |
| 417 | 37.47971435 |
| 418 | 37.76879932 |
| 419 | 37.99422901 |
| 420 | 38.30384897 |
| 421 | 38.68958152 |
| 422 | 39.0879526 |
| 423 | 39.42111231 |
| 424 | 39.72176954 |
| 425 | 40.13693778 |
| 426 | 40.46828425 |
| 427 | 40.70035149 |
| 428 | 41.13468931 |
| 429 | 41.31302158 |
| 430 | 41.74417977 |
| 431 | 42.33024774 |
| 432 | 42.67726419 |
| 433 | 42.82709685 |
| 434 | 43.3014327 |
| 435 | 43.63963746 |
| 436 | 44.00318533 |
| 437 | 44.37853157 |
| 438 | 44.62371228 |
| 439 | 45.08605578 |
| 440 | 45.31633393 |
| 441 | 45.61595221 |
| 442 | 46.05367317 |
| 443 | 46.29031653 |
| 444 | 46.61029233 |
| 445 | 46.88674368 |
| 446 | 47.11856161 |
| 447 | 47.40926976 |
| 448 | 47.60027302 |
| 449 | 47.83309781 |
| 450 | 48.19463075 |
| 451 | 48.44163701 |
| 452 | 48.64160583 |
| 453 | 48.83596531 |
| 454 | 49.00828107 |
| 455 | 49.28087968 |
| 456 | 49.54683384 |
| 457 | 49.67233092 |
| 458 | 49.90838573 |
| 459 | 50.14468141 |
| 460 | 50.40367427 |
| 461 | 50.66444983 |
| 462 | 50.74929703 |
| 463 | 50.71988507 |
| 464 | 50.84790673 |
| 465 | 50.99842038 |
| 466 | 51.2557445 |
| 467 | 51.2577705 |
| 468 | 51.26857718 |
| 469 | 51.39753233 |
| 470 | 51.34699382 |
| 471 | 51.27015335 |
| 472 | 51.1108684 |
| 473 | 51.13983328 |
| 474 | 51.17005058 |
| 475 | 51.16589324 |
| 476 | 51.0857339 |
| 477 | 51.05343627 |
| 478 | 51.06375135 |
| 479 | 51.02306375 |
| 480 | 51.04245077 |
| 481 | 51.10738923 |
| 482 | 51.12523652 |
| 483 | 51.13230981 |
| 484 | 51.28828273 |
| 485 | 50.81754489 |
| 486 | 51.73928913 |
| 487 | 52.21340557 |
| 488 | 51.74542471 |

-continued

| | |
|---|---|
| 489 | 51.78179865 |
| 490 | 51.90657325 |
| 491 | 51.98779226 |
| 492 | 51.9865365 |
| 493 | 52.01359901 |
| 494 | 52.12920118 |
| 495 | 52.11340653 |
| 496 | 51.91227268 |
| 497 | 52.04387546 |
| 498 | 51.78941768 |
| 499 | 51.7382666 |
| 500 | 51.50158588 |
| 501 | 51.19095477 |
| 502 | 50.91651083 |
| 503 | 50.65877615 |
| 504 | 50.35842556 |
| 505 | 50.01755161 |
| 506 | 49.59973921 |
| 507 | 49.24474856 |
| 508 | 48.82181173 |
| 509 | 48.56689424 |
| 510 | 48.15369141 |
| 511 | 47.88406813 |
| 512 | 47.62139199 |
| 513 | 47.44968041 |
| 514 | 47.34778256 |
| 515 | 47.22878071 |
| 516 | 47.15106189 |
| 517 | 47.15644627 |
| 518 | 47.23500375 |
| 519 | 47.42218076 |
| 520 | 47.59379283 |
| 521 | 47.66522807 |
| 522 | 47.96847225 |
| 523 | 48.16786285 |
| 524 | 48.42036693 |
| 525 | 48.60925228 |
| 526 | 48.87254774 |
| 527 | 49.14029069 |
| 528 | 49.28120433 |
| 529 | 49.44455809 |
| 530 | 49.52475222 |
| 531 | 49.60071947 |
| 532 | 49.62316186 |
| 533 | 49.59886788 |
| 534 | 49.49485439 |
| 535 | 49.39344518 |
| 536 | 49.23155757 |
| 537 | 48.93622997 |
| 538 | 48.64513078 |
| 539 | 48.33675979 |
| 540 | 47.91088874 |
| 541 | 47.48699707 |
| 542 | 47.06437534 |
| 543 | 46.61438661 |
| 544 | 46.11935334 |
| 545 | 45.63428679 |
| 546 | 45.11794672 |
| 547 | 44.62410424 |
| 548 | 44.28916116 |
| 549 | 43.90174713 |
| 550 | 43.48533873 |
| 551 | 43.1531623 |
| 552 | 42.94962397 |
| 553 | 42.81261641 |
| 554 | 42.70126215 |
| 555 | 42.63923257 |
| 556 | 42.74779661 |
| 557 | 42.81355655 |
| 558 | 42.99463521 |
| 559 | 43.15003531 |
| 560 | 43.37728285 |
| 561 | 43.73403514 |
| 562 | 44.06777974 |
| 563 | 44.34989006 |
| 564 | 44.67793363 |
| 565 | 45.06239974 |
| 566 | 45.36292896 |
| 567 | 45.65864409 |

-continued

| | |
|---|---|
| 568 | 45.94024409 |
| 569 | 46.13039355 |
| 570 | 46.45548625 |
| 571 | 46.65739818 |
| 572 | 46.86574468 |
| 573 | 46.88149305 |
| 574 | 46.99249908 |
| 575 | 47.19114882 |
| 576 | 47.19394685 |
| 577 | 46.95289021 |
| 578 | 47.3254339 |
| 579 | 47.06199836 |
| 580 | 47.00364509 |
| 581 | 46.62513578 |
| 582 | 47.13532647 |
| 583 | 46.92155686 |
| 584 | 46.37364251 |
| 585 | 46.44967191 |
| 586 | 46.43447646 |
| 587 | 46.09738207 |
| 588 | 46.04366239 |
| 589 | 45.95426868 |
| 590 | 45.73932639 |
| 591 | 45.53788741 |
| 592 | 45.21593932 |
| 593 | 45.1646353 |
| 594 | 45.14272233 |
| 595 | 44.91737024 |
| 596 | 44.89005672 |
| 597 | 44.6244962 |
| 598 | 44.36907978 |
| 599 | 44.40777666 |
| 600 | 44.27282529 |
| 601 | 44.196962 |
| 602 | 44.02937912 |
| 603 | 43.89345712 |
| 604 | 43.93096743 |
| 605 | 43.749884 |
| 606 | 43.70830499 |
| 607 | 43.65113846 |
| 608 | 43.59031343 |
| 609 | 43.49422022 |
| 610 | 43.48018257 |
| 611 | 43.45727368 |
| 612 | 43.43151561 |
| 613 | 43.3816647 |
| 614 | 43.39309771 |
| 615 | 43.39900595 |
| 616 | 43.42522152 |
| 617 | 43.41149212 |
| 618 | 43.5309114 |
| 619 | 43.46557676 |
| 620 | 43.47588623 |
| 621 | 43.56591149 |
| 622 | 43.56093708 |
| 623 | 43.68786608 |
| 624 | 43.77621539 |
| 625 | 43.82507612 |
| 626 | 43.9202607 |
| 627 | 43.94129079 |
| 628 | 44.08510482 |
| 629 | 44.1257826 |
| 630 | 44.29275976 |
| 631 | 44.39636878 |
| 632 | 44.54695426 |
| 633 | 44.69196542 |
| 634 | 44.8248476 |
| 635 | 44.90642312 |
| 636 | 45.03925063 |
| 637 | 45.27147674 |
| 638 | 45.45636261 |
| 639 | 45.6852214 |
| 640 | 45.8154225 |
| 641 | 46.04669573 |
| 642 | 46.27598614 |
| 643 | 46.42835889 |
| 644 | 46.66241878 |
| 645 | 46.90322007 |
| 646 | 47.28533674 |

-continued

| | |
|---|---|
| 647 | 47.51015231 |
| 648 | 47.71015217 |
| 649 | 47.96383775 |
| 650 | 48.35300247 |
| 651 | 48.62911032 |
| 652 | 48.95009426 |
| 653 | 49.18466089 |
| 654 | 49.69360534 |
| 655 | 48.72220946 |
| 656 | 50.01897947 |
| 657 | 51.63668291 |
| 658 | 51.19792472 |
| 659 | 51.51968397 |
| 660 | 51.92390148 |
| 661 | 52.40730449 |
| 662 | 52.82579372 |
| 663 | 53.250548 |
| 664 | 53.70159 |
| 665 | 54.21142272 |
| 666 | 54.75434387 |
| 667 | 55.21557701 |
| 668 | 55.72717749 |
| 669 | 56.23388555 |
| 670 | 56.88980521 |
| 671 | 57.4152792 |
| 672 | 57.96915171 |
| 673 | 58.59845449 |
| 674 | 59.20272925 |
| 675 | 59.82229886 |
| 676 | 60.43972495 |
| 677 | 61.0708989 |
| 678 | 61.71923469 |
| 679 | 62.4106236 |
| 680 | 63.07013506 |
| 681 | 63.73367667 |
| 682 | 64.40349207 |
| 683 | 65.06205693 |
| 684 | 65.73038704 |
| 685 | 66.40835304 |
| 686 | 67.13973722 |
| 687 | 67.80513555 |
| 688 | 68.48915906 |
| 689 | 69.15168103 |
| 690 | 69.83594554 |
| 691 | 70.45763269 |
| 692 | 71.11451866 |
| 693 | 71.79344999 |
| 694 | 72.47711238 |
| 695 | 73.08169843 |
| 696 | 73.71609041 |
| 697 | 74.25531403 |
| 698 | 74.98942093 |
| 699 | 75.56317601 |
| 700 | 76.15018309 |
| 701 | 76.73062887 |
| 702 | 77.2800235 |
| 703 | 77.88584058 |
| 704 | 78.39305198 |
| 705 | 78.94308092 |
| 706 | 79.39334283 |
| 707 | 79.94354339 |
| 708 | 80.50621887 |
| 709 | 80.9474412 |
| 710 | 81.39054552 |
| 711 | 81.90313287 |
| 712 | 82.357979 |
| 713 | 82.75118097 |
| 714 | 83.21128488 |
| 715 | 83.63390107 |
| 716 | 84.01400576 |
| 717 | 84.40213929 |
| 718 | 84.73901662 |
| 719 | 85.14040798 |
| 720 | 85.48849151 |
| 721 | 85.82744317 |
| 722 | 86.18193118 |
| 723 | 86.46627167 |
| 724 | 86.74945482 |
| 725 | 86.98866418 |

-continued

| | |
|---|---|
| 726 | 87.32800248 |
| 727 | 87.60650485 |
| 728 | 87.78617616 |
| 729 | 88.07155469 |
| 730 | 88.27097983 |
| 731 | 88.52876931 |
| 732 | 88.77113065 |
| 733 | 88.95123717 |
| 734 | 89.1350365 |
| 735 | 89.39201228 |
| 736 | 89.53188533 |
| 737 | 89.73757296 |
| 738 | 89.91727084 |
| 739 | 90.02889977 |
| 740 | 90.21393536 |
| 741 | 90.41761595 |
| 742 | 90.47799515 |
| 743 | 90.68127628 |
| 744 | 90.79764191 |
| 745 | 90.95888721 |
| 746 | 91.06281034 |
| 747 | 91.14343243 |
| 748 | 91.28544459 |
| 749 | 91.38954014 |
| 750 | 91.49797365 |

GREEN

| Wavelength $\lambda$ (nm) | Transmission factor $\tau\,2$ (%) |
|---|---|
| 350 | 0.14899478 |
| 351 | 0.19307862 |
| 352 | 0.24360347 |
| 353 | 0.33157605 |
| 354 | 0.40496553 |
| 355 | 0.51783277 |
| 356 | 0.67949269 |
| 357 | 0.87017322 |
| 358 | 1.11154255 |
| 359 | 1.41152548 |
| 360 | 1.78640852 |
| 361 | 2.16875379 |
| 362 | 2.70765511 |
| 363 | 3.16741351 |
| 364 | 3.636577 |
| 365 | 4.18171185 |
| 366 | 4.70786397 |
| 367 | 5.26999667 |
| 368 | 5.81153436 |
| 369 | 6.60475396 |
| 370 | 7.47641614 |
| 371 | 8.3472809 |
| 372 | 9.18857687 |
| 373 | 10.0106778 |
| 374 | 10.7023235 |
| 375 | 11.3986217 |
| 376 | 12.0003543 |
| 377 | 12.5758093 |
| 378 | 13.1024492 |
| 379 | 13.6240115 |
| 380 | 14.1031715 |
| 381 | 14.4542339 |
| 382 | 14.7753096 |
| 383 | 15.0952945 |
| 384 | 15.3456935 |
| 385 | 15.5457361 |
| 386 | 15.764406 |
| 387 | 15.9427868 |
| 388 | 16.0713303 |
| 389 | 16.1868993 |
| 390 | 16.272397 |
| 391 | 16.3476451 |
| 392 | 16.4424384 |
| 393 | 16.5666412 |
| 394 | 16.6134177 |
| 395 | 16.6486598 |
| 396 | 16.7674231 |
| 397 | 16.7616802 |

-continued

| | |
|---|---|
| 398 | 16.8440356 |
| 399 | 16.9610638 |
| 400 | 16.9747009 |
| 401 | 17.1297607 |
| 402 | 17.187447 |
| 403 | 17.3210806 |
| 404 | 17.469251 |
| 405 | 17.6123063 |
| 406 | 17.7924419 |
| 407 | 17.9129909 |
| 408 | 18.0896066 |
| 409 | 18.2994007 |
| 410 | 18.5403897 |
| 411 | 18.7487821 |
| 412 | 18.9380044 |
| 413 | 19.2306815 |
| 414 | 19.4752085 |
| 415 | 19.7351487 |
| 416 | 20.0198245 |
| 417 | 20.3374809 |
| 418 | 20.5851845 |
| 419 | 20.8798293 |
| 420 | 21.2136468 |
| 421 | 21.5152082 |
| 422 | 21.861776 |
| 423 | 22.2446301 |
| 424 | 22.5797307 |
| 425 | 22.9276314 |
| 426 | 23.3278195 |
| 427 | 23.6837618 |
| 428 | 24.0859321 |
| 429 | 24.4789616 |
| 430 | 24.9403236 |
| 431 | 25.4087629 |
| 432 | 25.8252495 |
| 433 | 26.2744558 |
| 434 | 26.7210878 |
| 435 | 27.147935 |
| 436 | 27.6901073 |
| 437 | 28.1609272 |
| 438 | 28.5985261 |
| 439 | 29.1439297 |
| 440 | 29.5833534 |
| 441 | 30.054603 |
| 442 | 30.6084791 |
| 443 | 31.057911 |
| 444 | 31.5359559 |
| 445 | 32.0118676 |
| 446 | 32.4406334 |
| 447 | 32.9517537 |
| 448 | 33.427884 |
| 449 | 33.8333898 |
| 450 | 34.3090722 |
| 451 | 34.7434969 |
| 452 | 35.1686688 |
| 453 | 35.6107715 |
| 454 | 36.0525729 |
| 455 | 36.4690106 |
| 456 | 36.8558461 |
| 457 | 37.2340277 |
| 458 | 37.6691576 |
| 459 | 38.0863662 |
| 460 | 38.4576615 |
| 461 | 38.9015382 |
| 462 | 39.2319029 |
| 463 | 39.5854087 |
| 464 | 39.9754434 |
| 465 | 40.3093512 |
| 466 | 40.7465844 |
| 467 | 40.9953685 |
| 468 | 41.4032957 |
| 469 | 41.7466548 |
| 470 | 42.0170429 |
| 471 | 42.344472 |
| 472 | 42.6012348 |
| 473 | 42.9489638 |
| 474 | 43.2614199 |
| 475 | 43.5258454 |
| 476 | 43.767853 |
| 477 | 44.0449481 |
| 478 | 44.3521301 |
| 479 | 44.5409876 |
| 480 | 44.8026076 |
| 481 | 45.0572545 |
| 482 | 45.2758511 |
| 483 | 45.4847199 |
| 484 | 45.7471614 |
| 485 | 45.7586149 |
| 486 | 46.3026178 |
| 487 | 46.4634439 |
| 488 | 46.4832419 |
| 489 | 46.7030133 |
| 490 | 46.8952901 |
| 491 | 47.0246026 |
| 492 | 47.197056 |
| 493 | 47.3119259 |
| 494 | 47.4689605 |
| 495 | 47.5167255 |
| 496 | 47.5734174 |
| 497 | 47.6989434 |
| 498 | 47.6719274 |
| 499 | 47.7640331 |
| 500 | 47.7543845 |
| 501 | 47.735303 |
| 502 | 47.7096283 |
| 503 | 47.6910883 |
| 504 | 47.6460775 |
| 505 | 47.6115632 |
| 506 | 47.4934627 |
| 507 | 47.4177032 |
| 508 | 47.3083937 |
| 509 | 47.2184108 |
| 510 | 47.067786 |
| 511 | 46.9586644 |
| 512 | 46.8626574 |
| 513 | 46.7594531 |
| 514 | 46.6627262 |
| 515 | 46.5158147 |
| 516 | 46.4508959 |
| 517 | 46.3055665 |
| 518 | 46.1240122 |
| 519 | 46.0471002 |
| 520 | 45.9374195 |
| 521 | 45.7574091 |
| 522 | 45.6946525 |
| 523 | 45.4888152 |
| 524 | 45.3986045 |
| 525 | 45.2766465 |
| 526 | 45.1111111 |
| 527 | 44.9594083 |
| 528 | 44.7572761 |
| 529 | 44.5661314 |
| 530 | 44.4088493 |
| 531 | 44.1531159 |
| 532 | 43.9334757 |
| 533 | 43.6963092 |
| 534 | 43.3973859 |
| 535 | 43.1504143 |
| 536 | 42.8975001 |
| 537 | 42.5630841 |
| 538 | 42.2483419 |
| 539 | 41.9269957 |
| 540 | 41.5564116 |
| 541 | 41.2197762 |
| 542 | 40.9003252 |
| 543 | 40.5401509 |
| 544 | 40.1746783 |
| 545 | 39.8090036 |
| 546 | 39.4729125 |
| 547 | 39.0761951 |
| 548 | 38.8202138 |
| 549 | 38.4691483 |
| 550 | 38.1275366 |
| 551 | 37.8077999 |
| 552 | 37.5343205 |
| 553 | 37.2489933 |
| 554 | 37.0118894 |
| 555 | 36.7552229 |

-continued

| | |
|---|---|
| 556 | 36.5656382 |
| 557 | 36.3238696 |
| 558 | 36.1707271 |
| 559 | 35.9319641 |
| 560 | 35.7946194 |
| 561 | 35.6751869 |
| 562 | 35.5132357 |
| 563 | 35.3567554 |
| 564 | 35.2486901 |
| 565 | 35.1682054 |
| 566 | 35.0333185 |
| 567 | 34.9110594 |
| 568 | 34.777617 |
| 569 | 34.6281038 |
| 570 | 34.5359137 |
| 571 | 34.4181112 |
| 572 | 34.2933298 |
| 573 | 34.1214634 |
| 574 | 34.0253915 |
| 575 | 33.9123835 |
| 576 | 33.7625863 |
| 577 | 33.5288209 |
| 578 | 33.5671286 |
| 579 | 33.2855623 |
| 580 | 33.1847747 |
| 581 | 32.9114019 |
| 582 | 33.0096195 |
| 583 | 32.7836591 |
| 584 | 32.5141618 |
| 585 | 32.4688555 |
| 586 | 32.3399896 |
| 587 | 32.1615944 |
| 588 | 32.0665338 |
| 589 | 31.9665592 |
| 590 | 31.8331153 |
| 591 | 31.7239748 |
| 592 | 31.5678965 |
| 593 | 31.5493933 |
| 594 | 31.4798439 |
| 595 | 31.4061716 |
| 596 | 31.3972074 |
| 597 | 31.3412734 |
| 598 | 31.2863322 |
| 599 | 31.3619959 |
| 600 | 31.3370067 |
| 601 | 31.3998274 |
| 602 | 31.4277652 |
| 603 | 31.5020415 |
| 604 | 31.662939 |
| 605 | 31.7204222 |
| 606 | 31.8503161 |
| 607 | 31.9980224 |
| 608 | 32.1666797 |
| 609 | 32.3307588 |
| 610 | 32.515804 |
| 611 | 32.7023392 |
| 612 | 32.924124 |
| 613 | 33.1098751 |
| 614 | 33.3539738 |
| 615 | 33.5910931 |
| 616 | 33.8397798 |
| 617 | 34.0826728 |
| 618 | 34.3604925 |
| 619 | 34.5728665 |
| 620 | 34.8513144 |
| 621 | 35.0580218 |
| 622 | 35.2900476 |
| 623 | 35.5877886 |
| 624 | 35.8437007 |
| 625 | 36.1193737 |
| 626 | 36.431951 |
| 627 | 36.6804796 |
| 628 | 36.9934445 |
| 629 | 37.2255254 |
| 630 | 37.5639218 |
| 631 | 37.8804315 |
| 632 | 38.1980143 |
| 633 | 38.5425426 |
| 634 | 38.889666 |

-continued

| | |
|---|---|
| 635 | 39.2333675 |
| 636 | 39.5763694 |
| 637 | 39.9570132 |
| 638 | 40.300589 |
| 639 | 40.6957043 |
| 640 | 41.0578917 |
| 641 | 41.4476875 |
| 642 | 41.7715054 |
| 643 | 42.1504863 |
| 644 | 42.6101229 |
| 645 | 42.989726 |
| 646 | 43.4678675 |
| 647 | 43.8723536 |
| 648 | 44.3154279 |
| 649 | 44.7639598 |
| 650 | 45.1800105 |
| 651 | 45.696258 |
| 652 | 46.1773186 |
| 653 | 46.6727691 |
| 654 | 47.27973 |
| 655 | 46.9639237 |
| 656 | 47.9617313 |
| 657 | 48.7063775 |
| 658 | 49.1300405 |
| 659 | 49.742735 |
| 660 | 50.2458676 |
| 661 | 50.7671308 |
| 662 | 51.3741746 |
| 663 | 51.9407793 |
| 664 | 52.508444 |
| 665 | 53.1365429 |
| 666 | 53.6787176 |
| 667 | 54.3030447 |
| 668 | 54.937046 |
| 669 | 55.5108772 |
| 670 | 56.1509649 |
| 671 | 56.7162993 |
| 672 | 57.3357784 |
| 673 | 57.981628 |
| 674 | 58.5902197 |
| 675 | 59.2053294 |
| 676 | 59.8437151 |
| 677 | 60.484734 |
| 678 | 61.1064475 |
| 679 | 61.7416012 |
| 680 | 62.4034975 |
| 681 | 63.0438262 |
| 682 | 63.6886275 |
| 683 | 64.2977932 |
| 684 | 64.9427265 |
| 685 | 65.5499235 |
| 686 | 66.2175939 |
| 687 | 66.8509486 |
| 688 | 67.4736163 |
| 689 | 68.0841405 |
| 690 | 68.7016976 |
| 691 | 69.3008077 |
| 692 | 69.9165028 |
| 693 | 70.5310077 |
| 694 | 71.1513823 |
| 695 | 71.7272665 |
| 696 | 72.2952691 |
| 697 | 72.827298 |
| 698 | 73.4454489 |
| 699 | 74.000728 |
| 700 | 74.5554574 |
| 701 | 75.121768 |
| 702 | 75.6159603 |
| 703 | 76.1598824 |
| 704 | 76.6686481 |
| 705 | 77.1813209 |
| 706 | 77.6353421 |
| 707 | 78.1213633 |
| 708 | 78.6268279 |
| 709 | 79.0806691 |
| 710 | 79.5056979 |
| 711 | 79.9721631 |
| 712 | 80.3767398 |
| 713 | 80.7940075 |

-continued

| | |
|---|---|
| 714 | 81.2139765 |
| 715 | 81.6058381 |
| 716 | 81.9891475 |
| 717 | 82.3541812 |
| 718 | 82.6603735 |
| 719 | 83.0517364 |
| 720 | 83.3927457 |
| 721 | 83.7193433 |
| 722 | 84.0213856 |
| 723 | 84.3078539 |
| 724 | 84.6224249 |
| 725 | 84.8749638 |
| 726 | 85.180053 |
| 727 | 85.4629646 |
| 728 | 85.6781166 |
| 729 | 85.9322964 |
| 730 | 86.1605488 |
| 731 | 86.4023082 |
| 732 | 86.6624425 |
| 733 | 86.8672604 |
| 734 | 87.0488562 |
| 735 | 87.2892745 |
| 736 | 87.486352 |
| 737 | 87.6877254 |
| 738 | 87.8920713 |
| 739 | 88.0371366 |
| 740 | 88.2031634 |
| 741 | 88.4257963 |
| 742 | 88.5351848 |
| 743 | 88.6953337 |
| 744 | 88.8668948 |
| 745 | 89.0120054 |
| 746 | 89.1366024 |
| 747 | 89.2584337 |
| 748 | 89.3874976 |
| 749 | 89.4856952 |
| 750 | 89.5900992 |

BROWN

| Wavelength λ (nm) | Transmission factor τ 3 (%) |
|---|---|
| 350 | 0.11858921 |
| 351 | 0.13166479 |
| 352 | 0.16038578 |
| 353 | 0.23249626 |
| 354 | 0.27983577 |
| 355 | 0.36079104 |
| 356 | 0.4728814 |
| 357 | 0.59939854 |
| 358 | 0.77679339 |
| 359 | 0.99369353 |
| 360 | 1.27734152 |
| 361 | 1.61186549 |
| 362 | 2.04253813 |
| 363 | 2.42335776 |
| 364 | 2.86878412 |
| 365 | 3.33963348 |
| 366 | 3.77023423 |
| 367 | 4.3092558 |
| 368 | 4.79261464 |
| 369 | 5.50546723 |
| 370 | 6.34038223 |
| 371 | 7.21308281 |
| 372 | 8.08238191 |
| 373 | 8.96985643 |
| 374 | 9.89080474 |
| 375 | 10.8286786 |
| 376 | 11.6565823 |
| 377 | 12.4568832 |
| 378 | 13.2412847 |
| 379 | 14.0192782 |
| 380 | 14.6892566 |
| 381 | 15.3218539 |
| 382 | 15.9272154 |
| 383 | 16.4782225 |
| 384 | 16.9699677 |
| 385 | 17.4163164 |

-continued

| | |
|---|---|
| 386 | 17.7949036 |
| 387 | 18.1668341 |
| 388 | 18.5001275 |
| 389 | 18.7074921 |
| 390 | 18.8941402 |
| 391 | 19.0895239 |
| 392 | 19.2080179 |
| 393 | 19.2989176 |
| 394 | 19.2688944 |
| 395 | 19.3036646 |
| 396 | 19.2781208 |
| 397 | 19.2290768 |
| 398 | 19.161256 |
| 399 | 19.0504117 |
| 400 | 18.8822778 |
| 401 | 18.803454 |
| 402 | 18.7049864 |
| 403 | 18.5849834 |
| 404 | 18.4474311 |
| 405 | 18.3687688 |
| 406 | 18.2828524 |
| 407 | 18.1713027 |
| 408 | 18.1441891 |
| 409 | 18.1173547 |
| 410 | 18.0811078 |
| 411 | 18.0555958 |
| 412 | 18.0401395 |
| 413 | 18.0546839 |
| 414 | 17.9979201 |
| 415 | 18.0101761 |
| 416 | 18.0347527 |
| 417 | 18.0166633 |
| 418 | 18.0253693 |
| 419 | 17.9717362 |
| 420 | 18.0062612 |
| 421 | 17.962425 |
| 422 | 17.9324726 |
| 423 | 17.8658506 |
| 424 | 17.8125356 |
| 425 | 17.7665179 |
| 426 | 17.7037389 |
| 427 | 17.6566451 |
| 428 | 17.5735579 |
| 429 | 17.4887108 |
| 430 | 17.3864347 |
| 431 | 17.2845669 |
| 432 | 17.1391296 |
| 433 | 17.1572421 |
| 434 | 17.0942134 |
| 435 | 16.8795446 |
| 436 | 16.8743191 |
| 437 | 16.7952083 |
| 438 | 16.7013882 |
| 439 | 16.6483674 |
| 440 | 16.5415587 |
| 441 | 16.5337872 |
| 442 | 16.4482887 |
| 443 | 16.3959633 |
| 444 | 16.3489375 |
| 445 | 16.2586814 |
| 446 | 16.2323184 |
| 447 | 16.1821725 |
| 448 | 16.2070659 |
| 449 | 16.1776958 |
| 450 | 16.1980643 |
| 451 | 16.1621789 |
| 452 | 16.2146482 |
| 453 | 16.1979932 |
| 454 | 16.2273289 |
| 455 | 16.3275904 |
| 456 | 16.354539 |
| 457 | 16.4361933 |
| 458 | 16.4835063 |
| 459 | 16.5563855 |
| 460 | 16.6086393 |
| 461 | 16.7347957 |
| 462 | 16.9084438 |
| 463 | 17.056792 |
| 464 | 17.2067819 |

-continued

| | |
|---|---|
| 465 | 17.2716668 |
| 466 | 17.4274109 |
| 467 | 17.5118452 |
| 468 | 17.7162613 |
| 469 | 17.8460494 |
| 470 | 18.0041262 |
| 471 | 18.2116891 |
| 472 | 18.3724398 |
| 473 | 18.5581491 |
| 474 | 18.6781839 |
| 475 | 18.8489702 |
| 476 | 18.95756 |
| 477 | 19.0886436 |
| 478 | 19.2995533 |
| 479 | 19.4346233 |
| 480 | 19.6500891 |
| 481 | 19.7765787 |
| 482 | 19.9317434 |
| 483 | 20.1206623 |
| 484 | 20.288192 |
| 485 | 20.6073913 |
| 486 | 20.6250019 |
| 487 | 20.3658146 |
| 488 | 20.790384 |
| 489 | 21.1197567 |
| 490 | 21.3134294 |
| 491 | 21.4676373 |
| 492 | 21.594016 |
| 493 | 21.7281515 |
| 494 | 21.8641765 |
| 495 | 21.9306297 |
| 496 | 22.024497 |
| 497 | 22.0263349 |
| 498 | 22.0210634 |
| 499 | 22.102889 |
| 500 | 22.0013428 |
| 501 | 21.951974 |
| 502 | 21.8665292 |
| 503 | 21.7617198 |
| 504 | 21.5515234 |
| 505 | 21.3937531 |
| 506 | 21.2250628 |
| 507 | 21.030669 |
| 508 | 20.8390623 |
| 509 | 20.6036357 |
| 510 | 20.3583922 |
| 511 | 20.1866033 |
| 512 | 19.9695514 |
| 513 | 19.8144839 |
| 514 | 19.646508 |
| 515 | 19.4991722 |
| 516 | 19.471189 |
| 517 | 19.3716917 |
| 518 | 19.3056146 |
| 519 | 19.3503491 |
| 520 | 19.3265259 |
| 521 | 19.4067327 |
| 522 | 19.5184929 |
| 523 | 19.6353374 |
| 524 | 19.7723232 |
| 525 | 19.940105 |
| 526 | 20.1694556 |
| 527 | 20.3378381 |
| 528 | 20.5424665 |
| 529 | 20.7580405 |
| 530 | 20.9180576 |
| 531 | 21.135995 |
| 532 | 21.3325334 |
| 533 | 21.5504822 |
| 534 | 21.6538938 |
| 535 | 21.8244587 |
| 536 | 21.9292813 |
| 537 | 22.0271088 |
| 538 | 22.1271218 |
| 539 | 22.1558081 |
| 540 | 22.194423 |
| 541 | 22.2017835 |
| 542 | 22.1834598 |
| 543 | 22.1069179 |

-continued

| | |
|---|---|
| 544 | 22.0132311 |
| 545 | 21.9009364 |
| 546 | 21.8292997 |
| 547 | 21.7510182 |
| 548 | 21.6495672 |
| 549 | 21.4886725 |
| 550 | 21.4358406 |
| 551 | 21.3524047 |
| 552 | 21.3177825 |
| 553 | 21.2828426 |
| 554 | 21.2663981 |
| 555 | 21.3390458 |
| 556 | 21.4084155 |
| 557 | 21.496507 |
| 558 | 21.6314618 |
| 559 | 21.8175587 |
| 560 | 22.070006 |
| 561 | 22.3071447 |
| 562 | 22.5355952 |
| 563 | 22.8371353 |
| 564 | 23.1686425 |
| 565 | 23.491546 |
| 566 | 23.8105302 |
| 567 | 24.153144 |
| 568 | 24.4388405 |
| 569 | 24.7890799 |
| 570 | 25.0389891 |
| 571 | 25.3006387 |
| 572 | 25.530969 |
| 573 | 25.758305 |
| 574 | 26.0789036 |
| 575 | 26.194495 |
| 576 | 26.3893492 |
| 577 | 26.6113525 |
| 578 | 26.8614002 |
| 579 | 26.7683648 |
| 580 | 27.1018325 |
| 581 | 27.2391193 |
| 582 | 27.4257801 |
| 583 | 27.1930411 |
| 584 | 27.5421999 |
| 585 | 27.7770123 |
| 586 | 27.6404133 |
| 587 | 27.8335521 |
| 588 | 27.9701843 |
| 589 | 28.0172717 |
| 590 | 28.23734 |
| 591 | 28.3816253 |
| 592 | 28.6224 |
| 593 | 28.931722 |
| 594 | 29.0533222 |
| 595 | 29.4171928 |
| 596 | 29.688389 |
| 597 | 30.0602793 |
| 598 | 30.408636 |
| 599 | 30.8234404 |
| 600 | 31.113066 |
| 601 | 31.4879328 |
| 602 | 31.7784982 |
| 603 | 32.1418257 |
| 604 | 32.394647 |
| 605 | 32.5610329 |
| 606 | 32.7525741 |
| 607 | 32.8649647 |
| 608 | 32.9391656 |
| 609 | 32.9121246 |
| 610 | 32.8995517 |
| 611 | 32.6836018 |
| 612 | 32.5185174 |
| 613 | 32.2178604 |
| 614 | 31.9006431 |
| 615 | 31.5463452 |
| 616 | 31.1355519 |
| 617 | 30.7172219 |
| 618 | 30.3530635 |
| 619 | 29.8225983 |
| 620 | 29.4024682 |
| 621 | 28.8365813 |
| 622 | 28.4184825 |

-continued

| | |
|---|---|
| 623 | 27.9870185 |
| 624 | 27.5590186 |
| 625 | 27.2083918 |
| 626 | 27.0242194 |
| 627 | 26.7628987 |
| 628 | 26.5097509 |
| 629 | 26.239054 |
| 630 | 26.0271855 |
| 631 | 25.8558343 |
| 632 | 25.730378 |
| 633 | 25.6902366 |
| 634 | 25.6957093 |
| 635 | 25.7386851 |
| 636 | 25.8415304 |
| 637 | 25.9609718 |
| 638 | 26.0699715 |
| 639 | 26.2823614 |
| 640 | 26.5294925 |
| 641 | 26.8863035 |
| 642 | 27.2796441 |
| 643 | 27.8484082 |
| 644 | 28.4768282 |
| 645 | 29.230904 |
| 646 | 30.0941614 |
| 647 | 31.0451601 |
| 648 | 32.2134743 |
| 649 | 33.4348582 |
| 650 | 34.8208685 |
| 651 | 36.2431583 |
| 652 | 37.9256264 |
| 653 | 39.664852 |
| 654 | 41.491307 |
| 655 | 43.3837605 |
| 656 | 45.4567619 |
| 657 | 45.9886925 |
| 658 | 49.1678149 |
| 659 | 51.6650382 |
| 660 | 53.844941 |
| 661 | 56.0419479 |
| 662 | 58.065722 |
| 663 | 60.1373501 |
| 664 | 62.1300327 |
| 665 | 64.1057763 |
| 666 | 65.9598517 |
| 667 | 67.7418849 |
| 668 | 69.5076223 |
| 669 | 71.1267003 |
| 670 | 72.7218255 |
| 671 | 74.1091946 |
| 672 | 75.5079414 |
| 673 | 76.7988993 |
| 674 | 77.9267277 |
| 675 | 79.0166166 |
| 676 | 80.0250398 |
| 677 | 80.9552627 |
| 678 | 81.8254735 |
| 679 | 82.642224 |
| 680 | 83.3570442 |
| 681 | 84.0293196 |
| 682 | 84.6553221 |
| 683 | 85.1452691 |
| 684 | 85.6318462 |
| 685 | 86.1236624 |
| 686 | 86.6129777 |
| 687 | 86.928132 |
| 688 | 87.2450077 |
| 689 | 87.553425 |
| 690 | 87.8359252 |
| 691 | 88.0901228 |
| 692 | 88.3596072 |
| 693 | 88.5721315 |
| 694 | 88.8050556 |
| 695 | 88.9254574 |
| 696 | 89.1009854 |
| 697 | 89.2429507 |
| 698 | 89.459957 |
| 699 | 89.5684612 |
| 700 | 89.6611477 |
| 701 | 89.7598431 |

-continued

| | |
|---|---|
| 702 | 89.8629883 |
| 703 | 90.001029 |
| 704 | 90.095548 |
| 705 | 90.1464078 |
| 706 | 90.1570979 |
| 707 | 90.223841 |
| 708 | 90.4209914 |
| 709 | 90.4213885 |
| 710 | 90.3898233 |
| 711 | 90.4517729 |
| 712 | 90.4706442 |
| 713 | 90.4970706 |
| 714 | 90.5925084 |
| 715 | 90.6100163 |
| 716 | 90.6454402 |
| 717 | 90.6627592 |
| 718 | 90.6133989 |
| 719 | 90.6490232 |
| 720 | 90.6181745 |
| 721 | 90.6233484 |
| 722 | 90.5992724 |
| 723 | 90.6102153 |
| 724 | 90.5734128 |
| 725 | 90.5813689 |
| 726 | 90.5976809 |
| 727 | 90.6784885 |
| 728 | 90.6040473 |
| 729 | 90.6006651 |
| 730 | 90.6026546 |
| 731 | 90.5915138 |
| 732 | 90.7097561 |
| 733 | 90.6404641 |
| 734 | 90.6225524 |
| 735 | 90.707565 |
| 736 | 90.6892418 |
| 737 | 90.7270874 |
| 738 | 90.7892682 |
| 739 | 90.6862546 |
| 740 | 90.7368501 |
| 741 | 90.8177819 |
| 742 | 90.7153336 |
| 743 | 90.7187202 |
| 744 | 90.759169 |
| 745 | 90.6872503 |
| 746 | 90.7420308 |
| 747 | 90.6593748 |
| 748 | 90.7332637 |
| 749 | 90.6844624 |
| 750 | 90.6486251 |

Figure 13:
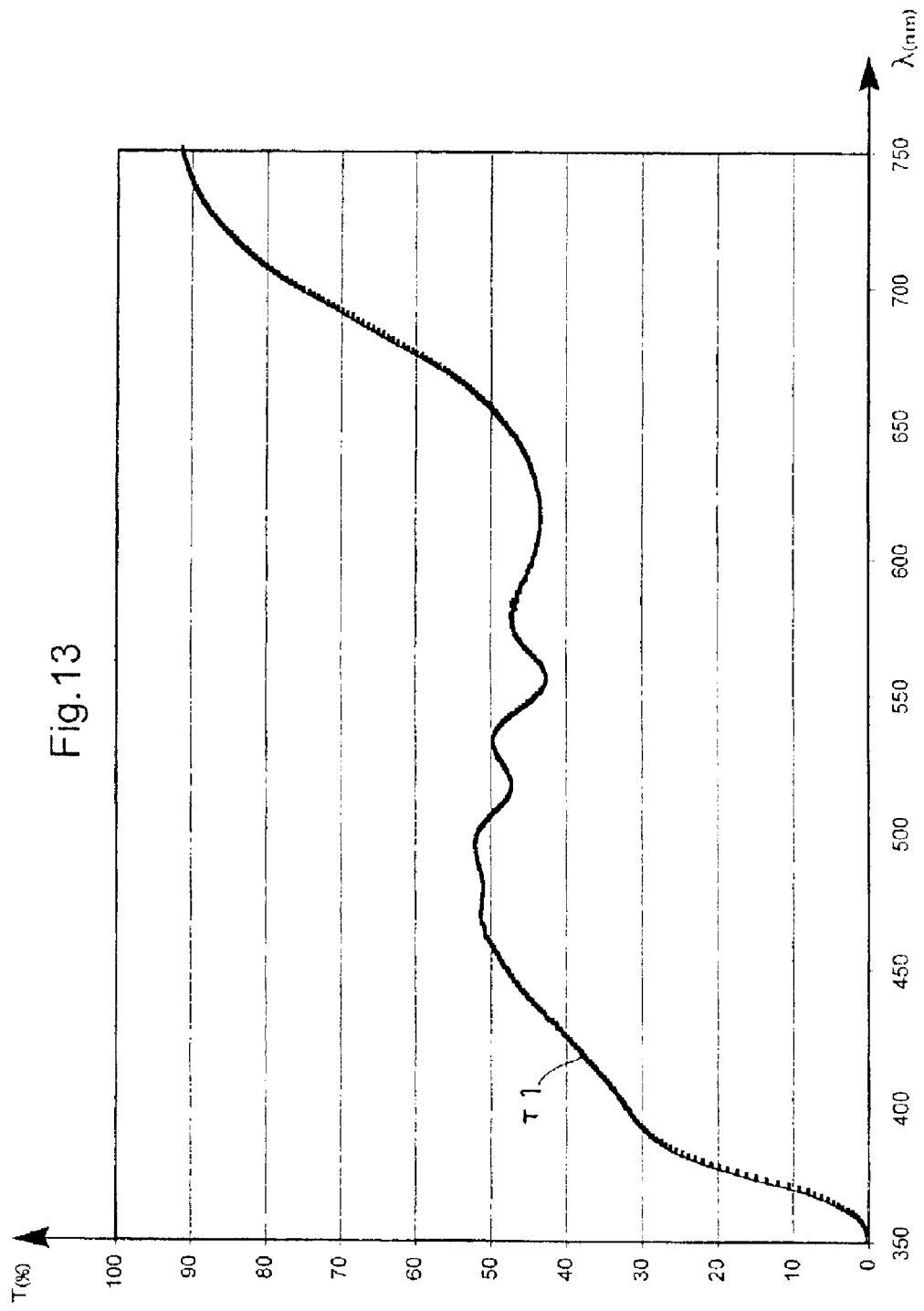
Figure 14:
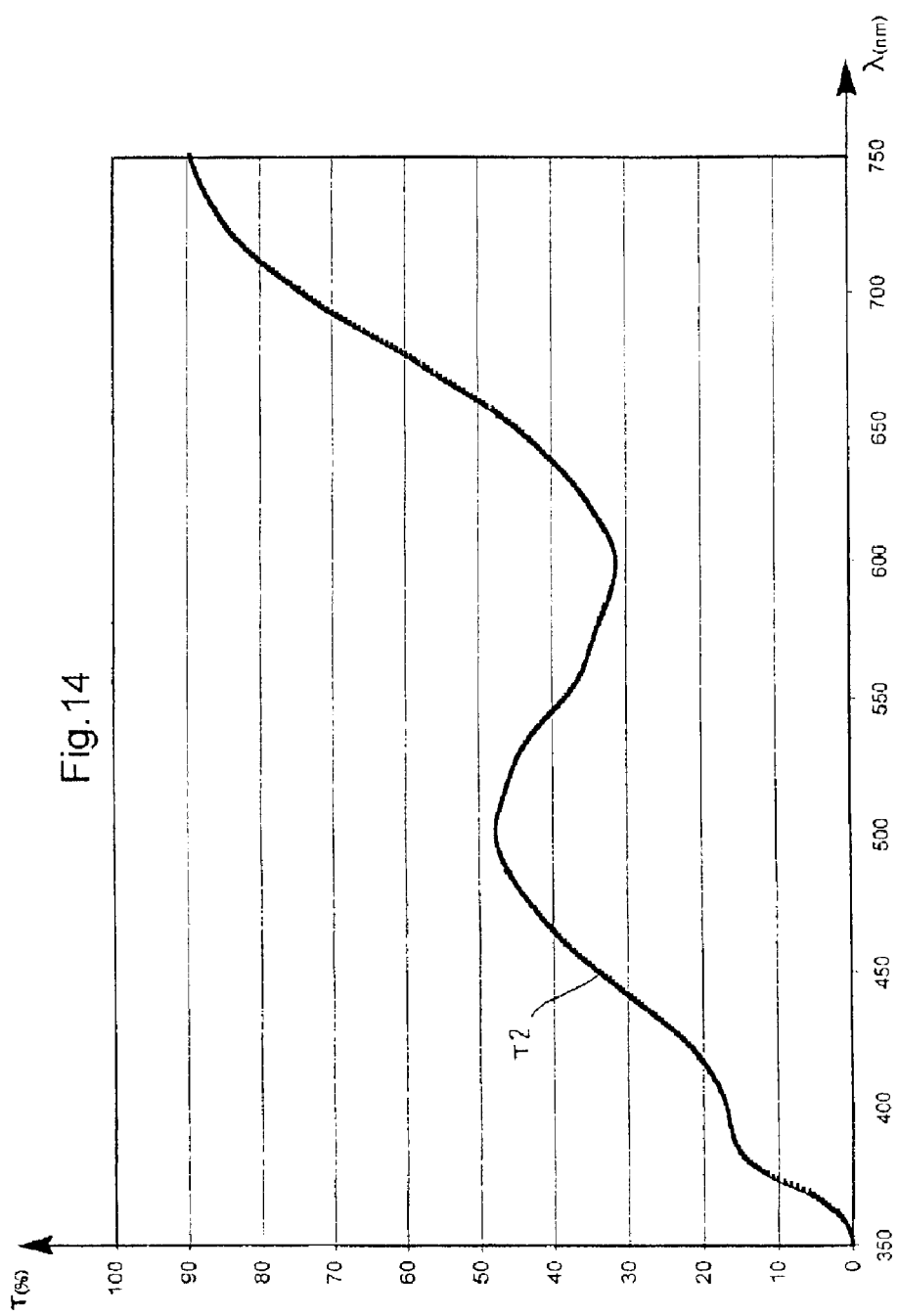

The spectral distributions of the transmission factors of the colors GRAY, GREEN and BROWN are shown in the FIGS. 13, 14 and 15 graphs, respectively.

The mean chromatic error values $\Delta E^*_m$ of the colors GRAY, GREEN and BROWN for the calorimetric deviation caused by a test palette of 127 samples defined in accordance with the first embodiment of the invention described above are respectively equal to 0.58945, 2.4204 and 3.4606.

If the test value $\Delta E_o$ is chosen to be equal to 5, it is found that the values of these mean chromatic errors are all less than the test value, and so the colors GRAY, GREEN and BROWN are accepted.

However, if the test value $\Delta E_o$ is instead chosen to be less than 5, for example equal to 0.5, it is necessary to measure the angular distribution corresponding to each of these colors.

Calculated in the manner previously defined, for the axis $a^*$ of the space CIELAB, the standard deviations of the GRAY, GREEN and BROWN colors are respectively equal to 51.454°, 40.622° and 36.901°, and are therefore all less than 55°. The angular distribution is therefore uniform for each of these colors.

There is claimed:

1. A method of obtaining a range of colors, including the following steps:

selecting a test color from a predetermined set of colors, selecting a test palette comprising a plurality of color samples, measuring the real color of each sample when illuminated by a white light source, measuring the apparent color of each sample when illuminated by a test source formed by said white light source filtered by said test color, measuring the chromatic error between the real color and the apparent color of each sample, taking account of chromatic adaptation, measuring the mean chromatic error for all the chromatic errors, comparing the mean, chromatic error to a test value, and adding the test color to the range if the mean chromatic error is less than or equal to said test value.

2. The method claimed in claim 1 wherein said test color is added to said range if and only if each chromatic error is less than or equal to said test value.

3. A method claimed in claim 1, which includes the following steps if at least one chromatic error is greater than said test value:

measuring the angular distribution of the colorimetric deviations between the real color and the apparent color of each sample, and adding said test color to said range if said angular distribution is uniform.

4. The method claimed in claim 1 wherein said set comprises the Munsell atlas.

5. The method claimed in claim 1 wherein said test palette comprises a plurality of color samples chosen front the Munsell atlas.

6. The method claimed in claim 1 wherein said test palette comprises a plurality of samples whose colors are most representative of the Munsell space.

7. The method claimed in claim 1 wherein said apparent color and said real color are measured by calculating their coordinates in a predetermined chromatic space.

8. The method claimed in claim 7 wherein said chromatic space is the CIELAB space.

9. A range of more than two colors obtained by the method claimed in claim 1.

10. A method of obtaining a colored ophthalmic lens, including a step of selecting a color obtained by a method as claimed in claim 1.

* * * * *